US007163928B2

(12) United States Patent
Cristalli et al.

(10) Patent No.: US 7,163,928 B2
(45) Date of Patent: Jan. 16, 2007

(54) PARTIAL AND FULL AGONISTS OF $A_1$ ADENOSINE RECEPTORS

(75) Inventors: Gloria Cristalli, Camerino (IT); Venkata Palle, Gurgaon (IN); Jeff Zablocki, Mountain View, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 198 days.

(21) Appl. No.: 10/770,542

(22) Filed: Feb. 2, 2004

(65) Prior Publication Data

US 2004/0198691 A1    Oct. 7, 2004

Related U.S. Application Data

(60) Provisional application No. 60/444,526, filed on Feb. 3, 2003.

(51) Int. Cl.
*A01N 43/04* (2006.01)
*A61K 31/70* (2006.01)
*C07H 19/00* (2006.01)
*C07H 19/22* (2006.01)
*C07H 19/167* (2006.01)

(52) U.S. Cl. .................. 514/45; 514/46; 536/27.1; 536/27.13; 536/27.2; 536/27.21; 536/27.6; 536/27.62

(58) Field of Classification Search ............. 536/27.1, 536/27.13, 27.2, 27.21; 514/45, 46
See application file for complete search history.

(56) References Cited

U.S. PATENT DOCUMENTS

| 5,578,582 | A | 11/1996 | Knutsen et al. |
| 5,789,416 | A | 8/1998 | Lum et al. |
| 6,211,165 | B1 * | 4/2001 | Liang et al. ............... 514/46 |
| 6,258,793 | B1 | 7/2001 | Palle et al. |
| 2003/0050275 | A1 | 3/2003 | Elzein et al. |

FOREIGN PATENT DOCUMENTS

| EP | 0181129 | 5/1986 |
| WO | WO 98/01459 A | 1/1998 |
| WO | WO 99/24449 | 5/1999 |
| WO | WO 99/24450 | 5/1999 |
| WO | WO 99/24451 | 5/1999 |
| WO | WO 99/67262 | 12/1999 |
| WO | WO 01/40243 | 6/2001 |

OTHER PUBLICATIONS

Dalpiaz et al., "Thermodynamic In Vitro Studies as a Method to Investigate Behavior of Adenosine A1 Receptor Ligands", Pharmaceutical Research, vol. 16, No. 7, pp. 1054-1058, 1999.*
Ghosal et al., 3'-Deoxyribonucleosides and their derivatives as anti-amoebic agents, International Journal of Pharmaceutics, 194, pp. 15-20, 2000).*
Charubala et al., "Inhibition of HIV-1 Replication by Chemically Synthesized, Nuclease-resistant, Nontoxic (2'à5')-Oligoadenylate Agonists", Helvetica Chimica Acta, vol. 85, pp. 2284-2299, 2002.*
Van der Wenden et al., "Ribose-modified Adenosine Analogs as Potential Partial Agonists for the Adenosine Receptor", Journal of Medicinal Chemistry, 38(20), pp. 4000-4006, 1995.*
R.M. Smejkal et al. (1989) "Muscarinic receptor subtype specificity of 5'(isobutylthio)-adenosine (SIBA) and its analogues," *Gen. Pharmac.*, 20(3):385-392, XP008022164.
Van Der Wenden, E. et al: "5'-Substituted adenosine analogs as new high-affinity partial agonists for the adenosine A1 receptor", J. Med Chem, 1998, 41, pp. 102-108.
Tilburg, E. et al: "N6.5'-Disubstituted adenosine derivatives as partial agonists for the human adenosine A3 receptor", J. Med. Chem, 1999, 42, pp. 1393-1400.
Mathe et al: "1,2-Di-*O*-acetyl-5-*O*-benzoyl-3-deoxy-L-*erythro*-pentofuranose, a convenient precursor for stereospecific synthesis of nucleoside analogues with the unnatural β-L-configuration", Carbohydrate Research, 2000, 323, pp. 226-229.
*Journal of Medicinal Chemistry*, "Ribose-Modified Adenosine Analogs as Potential Partial Agonists for the Adenosine Receptor", 38(20), 4000-6, van der Wenden, et al., 1995.
*Journal of Medicinal Chemistry*, "3'-Deoxynucleosides. II Purine 3'-Deoxynucleosides", 8(5), 659-53, Walton, et al., 1965.
*Helvetica Chimica Acta*, "Nucleotides. Part LXX Inhibition of HIV-1 Replication by Chemically Synthesized, Nuclease-Resistant, Nontoxic (2'-5')-Oligoadenylate Agonists", 2284-2289, Charubala, et al., 2002.
*Journal of Medicinal Chemistry*, "Structure-Activity Relationships of 9-Alkyladenine and Ribose-Modified Adenosine Derivatives at Rat A3 Adenosine Receptors", 38(10), 1720-35, Jacobson, et al., 1995.

* cited by examiner

*Primary Examiner*—Shaojia Anna Jiang
*Assistant Examiner*—Traviss C. McIntosh, III
(74) *Attorney, Agent, or Firm*—Brian Lewis; Pauline Ann Clarke; J. Elin Hartrum

(57) ABSTRACT

Disclosed are novel compounds that are partial and full $A_1$ adenosine receptor agonists, useful for treating various disease states, in particular tachycardia and atrial flutter, angina, and myocardial infarction.

15 Claims, No Drawings

PARTIAL AND FULL AGONISTS OF $A_1$ ADENOSINE RECEPTORS

Priority is claimed to U.S. Provisional Patent Application Ser. No. 60/444,526, filed Feb.3, 2003, the complete disclosure of which is hereby incorporated by reference.

FIELD OF THE INVENTION

The present invention relates to novel compounds that are partial or full $A_1$ adenosine receptor agonists, and to their use in treating mammals for various disease states, including modifying cardiac activity, in particular treatment of arrhythmia. The compounds are also useful for treating CNS disorders, diabetic disorders, obesity, and modifying adipocyte function. The invention also relates to methods for their preparation, and to pharmaceutical compositions containing such compounds.

BACKGROUND

Adenosine is a naturally occurring nucleoside, which exerts its biological effects by interacting with a family of adenosine receptors known as $A_1$, $A_{2a}$, $A_{2b}$, and $A_3$, all of which modulate important physiological processes. For example, $A_{2A}$ adenosine receptors modulate coronary vasodilation, $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, *Drug Dev Res* 45:198; Feoktistov et al., *Trends Pharmacol Sci* 19:148–153), and $A_3$ adenosine receptors modulate cell proliferation processes.

The $A_1$ adenosine receptor mediates two distinct physiological responses. Inhibition of the cardiostimulatory effects of catecholamine is mediated via the inhibition of adenylate cyclase, whereas the direct effects to slow the heart rate (HR) and to prolong impulse propagation through the AV node are due in great part to activation of $I_{KAdo}$. (B. Lerman and L. Belardinelli *Circulation*, Vol. 83 (1991), P 1499–1509 and J. C. Shryock and L. Belardinelli *The Am. J Cardiology*, Vol. 79 (1997) P 2–10). Stimulation of the $A_1$ adenosine receptor shortens the duration and decreases the amplitude of the action potential of AV nodal cells, and hence prolongs the refractory period of the AV nodal cell. Thus, stimulation of $A_1$ receptors provides a method of treating supraventricular tachycardias, including termination of nodal re-entrant tachycardias, and control of ventricular rate during atrial fibrillation and flutter.

Accordingly, $A_1$ adenosine receptor agonists are useful in the treatment of acute and chronic disorders of heart rhythm, especially those diseases characterized by rapid heart rate, in which the rate is driven by abnormalities in the sinoatrial, atria, and AV nodal tissues. Such disorders include, but are not limited to, atrial fibrillation, supraventricular tachycardia and atrial flutter. Exposure to $A_1$ agonists causes a reduction in the heart rate and a regularization of the abnormal rhythm, thereby improving cardiovascular function.

$A_1$ adenosine receptor agonists, through their ability to inhibit the effects of catecholamines, decrease cellular cAMP, and thus have beneficial effects in the failing heart where increased sympathetic tone increases cellular cAMP levels. The latter condition has been shown to be associated with increased likelihood of ventricular arrhythmias and sudden death. See, for example, B. Lerman and L. Belardinelli *Circulation*, Vol. 83 (1991), P 1499–1509 and J. C. Shryock and L. Belardinelli, *Am. J Cardiology*, Vol. 79 (1997) P 2–10.

$A_1$ adenosine receptor agonists, as a result of their inhibitory action on cyclic AMP generation, have anti-lipolytic effects in adipocytes that leads to a decreased release of non-esterified fatty acids (NEFA) (E. A. van Schaick et al J. Pharmacokinetics and Biopharmaceutics, Vol. 25 (1997) p 673–694 and P. Strong *Clinical Science* Vol. 84 (1993) p. 663–669). Non-insulin-dependent diabetes mellitus (NIDDM) is characterized by an insulin resistance that results in hyperglycemia. Factors contributing to the observed hyperglycemia are a lack of normal glucose uptake and activation of skeletal muscle glycogen synthase (GS). Elevated levels of NEFA have been shown to inhibit insulin-stimulated glucose uptake and glycogen synthesis (D. Thiebaud et al *Metab. Clin. Exp.* Vol. 31 (1982) p 1128–1136 and G. Boden et al *J. Clin. Invest.* Vol. 93 (1994) p 2438–2446). A glucose fatty acid cycle was proposed by P. J. Randle as early as 1963 (P. J. Randle et al Lancet (1963) p. 785–789). A tenet of this hypothesis would be that limiting the supply of fatty acids to the peripheral tissues should promote carbohydrate utilization (P. Strong et al *Clinical Science* Vol. 84 (1993) p. 663–669).

The benefit of $A_1$ adenosine receptor agonists in central nervous disorders has been reviewed (L. J. S. Knutsen and T. F. Murray In Purinergic Approaches in Experimental Therapeutics, Eds. K. A. Jacobson and M. F. Jarvis (1997) Wiley-Liss, N. Y., P 423–470). Briefly, based on experimental models of epilepsy, a mixed $A_{2A}$: $A_1$ agonist, metrifudil, has been shown to be a potent anticonvulsant against seizures induced by the inverse benzodiazepine agonist methyl 6,7-dimethoxy-4-ethyl-beta-carboline-3-carboxylate (DMCM, H. Klitgaard *Eur. J. Pharmacol.* (1993) Vol. 224 p. 221–228). In other studies using CGS 21680, an $A_{2A}$ agonist, it was concluded that the anticonvulsant activity was attributed to activation of $A_1$ adenosine receptor agonists (G. Zhang et al. *Eur. J. Pharmacol.* Vol. 255 (1994) p. 239–243). Furthermore, $A_1$ adenosine receptor agonists have been shown to have anticonvulsant activity in the DMCM model (L. J. S. Knutsen In Adenosine and Adenine Nucleotides: From Molecular Biology to Integrative Physiology; eds. L. Belardinelli and A. Pelleg, Kluwer: Boston, 1995, pp 479–487). A second area where an $A_1$ adenosine agonist has a benefit is in animal models of forebrain ischemia as demonstrated by Knutsen et al (*J. Med. Chem.* Vol. 42 (1999) p. 3463–3477). The benefit in neuroprotection is believed to be in part due to the inhibition of the release of excitatory amino acids (ibid).

Adenosine itself has proven effective in treating disease states related to the $A_1$ adenosine receptor, for example in terminating paroxysmal supraventricular tachycardia. However, these effects are short-lived because adenosine's half-life is less than 10 sec. Additionally, as adenosine acts indiscriminately on the $A_{2A}$, $A_{2B}$, and the $A_3$ adenosine receptor subtypes, it also provides direct effects on sympathetic tone, coronary vasodilatation, systemic vasodilatation and mast cell degranulation.

Accordingly, it is an object of this invention to provide compounds that are potent full $A_1$ adenosine receptor agonists or partial $A_1$ receptor agonists with a half life greater than that of adenosine, and that are selective for the $A_1$ adenosine receptor, which will ensure that undesired side effects related to stimulation or antagonism of the other adenosine receptors are avoided.

SUMMARY OF THE INVENTION

It is an object of this invention to provide compounds that are partial or full, $A_1$ adenosine receptor agonists. Accordingly, in a first aspect, the invention relates to compounds of Formula I:

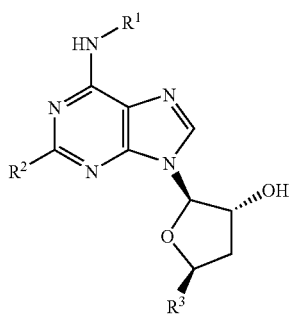

wherein:
- $R^1$ is optionally substituted alkyl, optionally substituted cycloalkyl, optionally substituted heterocyclyl, optionally substituted aryl, or optionally substituted heteroaryl;
- $R^2$ is hydrogen, halo, trifluoromethyl, optionally substituted acyl, or cyano;
- $R^3$ is hydroxymethyl or $R^4R^5N(O)C$—, in which $R^4$ and $R^5$ are independently hydrogen or optionally substituted alkyl.

A second aspect of this invention relates to pharmaceutical formulations, comprising a therapeutically effective amount of a compound of Formula I and at least one pharmaceutically acceptable excipient.

A third aspect of this invention relates to a method of using the compounds of Formula I in the treatment of a disease or condition in a mammal that can be treated with a partial or full selective $A_1$ adenosine receptor agonists. Such diseases include atrial fibrillation, and atrial flutter, congestive heart failure, epilepsy, stroke, diabetes, obesity, ischemia, including stable angina, unstable angina and myocardial infarction. The compounds of the invention also have anti-lipolytic effects, and are therefore useful for treating metabolic disorders, including type II diabetes. The compounds of the invention are also useful in protecting tissues being maintained for transplantation.

Preferred definitions of $R^1$ include optionally substituted cycloalkyl, for example optionally substituted cyclopentyl or optionally substituted cyclohexyl. More preferred definitions of $R^1$ include 2-hydroxycyclopentyl, 4-hydroxycyclohexyl, and 2-hydroxycyclohexyl. Another preferred definition of $R^1$ is optionally substituted pyrrolidinyl, for example pyrrolidinyl substituted with R"X, wherein X is carbonyl or sulphonyl and R" is optionally substituted aryl or optionally substituted alkyl. Preferred examples of R"X include benzoyl, 4-fluorobenzoyl, 4-cyanobenzoyl, 4-methoxybenzoyl, 4-trifluorobenzoyl, 4-ethylbenzoyl, 2-naphthoyl, 3-naphthoyl, 2-fluorobenzoyl, 3-fluorobenzoyl, 1-benzenesulfonyl, acetyl, 2-methylpropanoyl, heptanoyl, and the like.

Preferred embodiments of the invention include, but are not limited to:
- 2-{6-[((3R)oxolan-3-yl)amino]purin-9-yl}(5S,2R,3R)-5-(hydroxymethyl)oxolan-3-ol;
- 2-{6-[((1R)-4-hydroxycyclohexyl)amino]purin-9-yl}(5S, 2R,3R)-5-(hydroxymethyl)oxolan-3-ol;
- 2-{6-[((1R)-2-hydroxycyclohexyl)amino]purin-9-yl}(5S, 2R,3R)-5-(hydroxymethyl)oxolan-3-ol;
- 2-{6-[((3R)pyrrolidin-3-yl)amino]purin-9-yl}(5S,2R, 3R)-5-(hydroxymethyl)oxolan-3-ol;
- (5S,2R,3R)-2-{6-[((1S,2S)-2-hydroxycyclopentyl) amino]purin-9-yl}-5-(hydroxymethyl)oxolan-3-ol;
- (3R)-3-({9-[(5S,2R,3R)-3-hydroxy-5-(hydroxymethyl) oxolan-2-yl]purin-6-yl}amino)pyrrolidinyl phenyl ketone;
- (3R)-3-({9-[(5S,2R,3R)-3-hydroxy-5-(hydroxymethyl) oxolan-2-yl]purin-6-yl}amino)pyrrolidinyl 4-fluorophenyl ketone;
- 4-{[(3R)-3-({9-[(5S,2R,3R)-3-hydroxy-5-(hydroxymethyl)oxolan-2-yl]purin-6-yl}amino)pyrrolidinyl] carbonyl}benzenecarbonitrile;
- (3R)-3-({9-[(5S,2R,3R)-3-hydroxy-5-(hydroxymethyl) oxolan-2-yl]purin-6-yl}amino)pyrrolidinyl 4-methoxyphenyl ketone;
- (3R)-3-({9-[(5S,2R,3R)-3-hydroxy-5-(hydroxymethyl) oxolan-2-yl]purin-6-yl}amino)pyrrolidinyl 4-(trifluoromethyl)phenyl ketone;
- (3R)-3-({9-[(5S,2R,3R)-3-hydroxy-5-(hydroxymethyl) oxolan-2-yl]purin-6-yl}amino)pyrrolidinyl 4-ethylphenyl ketone;
- (3R)-3-({9-[(5S,2R,3R)-3-hydroxy-5-(hydroxymethyl) oxolan-2-yl]purin-6-yl}amino)pyrrolidinyl 2-naphthyl ketone;
- (3R)-3-({9-[(5S,2R,3R)-3-hydroxy-5-(hydroxymethyl) oxolan-2-yl]purin-6-yl}amino)pyrrolidinyl 3-fluorophenyl ketone;
- (3R)-3-({9-[(5S,2R,3R)-3-hydroxy-5-(hydroxymethyl) oxolan-2-yl]purin-6-yl}amino)pyrrolidinyl naphthyl ketone;
- (3R)-3-({9-[(5S,2R,3R)-3-hydroxy-5-(hydroxymethyl) oxolan-2-yl]purin-6-yl}amino)pyrrolidinyl 2-fluorophenyl ketone;
- (3R)-3-({9-[(5S,2R,3R)-3-hydroxy-5-(hydroxymethyl) oxolan-2-yl]purin-6-yl}amino)-1-(phenylsulfonyl)pyrrolidine;
- (3R)-3-({9-[(5S,2R,3R)-3-hydroxy-5-(hydroxymethyl) oxolan-2-yl]purin-6-yl}amino)-1-acetylpyrrolidine;
- 1-[(3R)-3-({9-[(5S,2R,3R)-3-hydroxy-5-(hydroxymethyl)oxolan-2-yl]purin-6-yl}amino)pyrrolidinyl]-2-methylpropan-1-one;
- 1-[(3R)-3-({9-[(5S,2R,3R)-3-hydroxy-5-(hydroxymethyl)oxolan-2-yl]purin-6-yl}amino)pyrrolidinyl]heptan-1-one;
- 2-{6-[((3R)pyrrolidin-3-yl)amino]-2-chloropurin-9-yl} (5S,2R,3R)-5-(hydroxymethyl)oxolan-3-ol;
- 2-{6-[((1R)-2-hydroxycyclopentyl)amino]-2-chloropurin-9-yl}(5S,2R,3R)-5-(hydroxymethyl)oxolan-3-ol;
- (3R)-3-({9-[(5S,2R,3R)-3-hydroxy-5-(hydroxymethyl) oxolan-2-yl]-2-chloropurin-6-yl}amino)-1-acetylpyrrolidine; and
- 1-[(3R)-3-({9-[(5S,2R,3R)-3-hydroxy-5-(hydroxymethyl)oxolan-2-yl]-2-chloropurin-6-yl}amino)pyrrolidinyl]heptan-1-one.

DEFINITIONS AND GENERAL PARAMETERS

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
1) an alkyl group as defined above, having from 1 to 5 substituents, for example 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
2) an alkyl group as defined above that is interrupted by 1–5 atoms or groups independently chosen from oxygen, sulfur and —NR$_a$—, where R$_a$ is chosen from hydrogen, alkyl, cycloalkyl, alkenyl, cycloalkenyl, alkynyl, aryl, heteroaryl and heterocyclyl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
3) an alkyl group as defined above that has both from 1 to 5 substituents as defined above and is also interrupted by 1–5 atoms or groups as defined above.

The term "lower alkyl" refers to a monoradical branched or unbranched saturated hydrocarbon chain having from 1 to 6 carbon atoms. Groups such as methyl, ethyl, n-propyl, isopropyl, n-butyl, iso-butyl, t-butyl, n-hexyl, and the like exemplify this term.

The term "substituted lower alkyl" refers to lower alkyl as defined above having 1 to 5 substituents, for example 1 to 3 substituents, as defined for substituted alkyl, or a lower alkyl group as defined above that is interrupted by 1–5 atoms as defined for substituted alkyl, or a lower alkyl group as defined above that has both from 1 to 5 substituents as defined above and is also interrupted by 1–5 atoms as defined above.

The term "alkylene" refers to a diradical of a branched or unbranched saturated hydrocarbon chain, for example having from 1 to 20 carbon atoms, for example 1–10 carbon atoms, more for example 1–6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, for example having from 1 to 6 carbon atoms.

The term "substituted alkylene" refers to:
(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
(2) an alkylene group as defined above that is interrupted by 1–5 atoms or groups independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or
(3) an alkylene group as defined above that has both from 1 to 5 substituents as defined above and is also interrupted by 1–20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, isopropoxy, n-butoxy, tert-butoxy, sec-butoxy, n-pentoxy, n-hexoxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group for example having from 2 to 20 carbon atoms, more for example 2 to 10 carbon atoms and even more for example 2 to 6 carbon atoms and having 1–6, for example 1, double bond (vinyl). Preferred alkenyl groups include ethenyl or vinyl (—CH═CH$_2$), 1-propylene or allyl (—CH$_2$CH═CH$_2$), isopropylene, (—C(CH$_3$)═CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and for example I to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, for example having from 2 to 20 carbon atoms, more for example 2 to 10 carbon atoms and even more for example 2 to 6 carbon atoms and having at least 1 and for example from 1–6 sites of acetylene (triple bond) unsaturation. Preferred alkynyl groups include ethynyl, (—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having from 1 to 5 substituents, and for example 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, CF$_3$, amino, substituted amino, cyano, or —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, for example 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1 to 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y—Z, in which Y is optionally substituted alkylene and Z is alkenyl, cycloalkenyl, or alkynyl, Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1]heptane, 1,3,3-trimethylbicyclo[2.2.1]hept-2-yl, (2,3,3-trimethylbicyclo[2.2.1]hept-2-yl), or cyclic alkyl groups to which is fused an aryl group, for example indane, and the like.

The term "substituted cycloalkyl" refers to cycloalkyl groups having from 1 to 5 substituents, and for example 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, for example 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazolyl, or benzothienyl). Examples of heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, for example 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and for example 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Heterocyclic groups can have a single ring or multiple condensed rings. Preferred heterocyclics include tetrahydrofuranyl, morpholino, and piperidinyl.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, and prodrugs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R-S system. When the compound is a pure enantiomer, the stereochemistry at each chiral carbon may be specified as either R or S. Resolved compounds whose absolute configuration is unknown are designated (+) or (−) depending on the direction (dextro- or laevorotary) in which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A compound that is an agonist with high intrinsic efficacy evokes the maximal effect of which the biological system is capable. These compounds are known as "full agonists". They are able to elicit the maximum possible effect without occupying all the receptors, if the efficiency of coupling to the effector process is high. In contrast, "partial agonists" evoke a response but cannot evoke the maximal response of which the biological system is capable. They may have reasonable affinity but low intrinsic efficacy. Partial $A_1$ adenosine agonists may have an added benefit for chronic therapy because they will be less likely to induce desensitization of the $A_1$ receptor (R. B. Clark, B. J. Knoll, R. Barber TiPS, Vol. 20 (1999) p. 279–286), and less likely to cause side effects.

NOMENCLATURE

The naming and numbering of the compounds of the invention is illustrated with a representative compound of Formula I in which $R^1$ is 4-hydroxycyclohexyl, $R^2$ is hydrogen, and $R^3$ is hydroxymethyl:

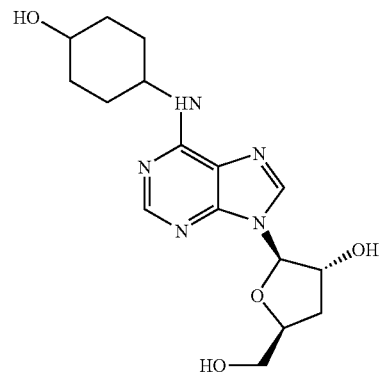

which is named (5S,2R,3R)-2-{6-[(4-hydroxycyclohexyl)amino]purin-9-yl}-5-(hydroxymethyl)oxolan-3-ol.

The Compounds of the Invention

As presented in the Summary of the Invention, the invention relates to compounds having the structure of Formula I:

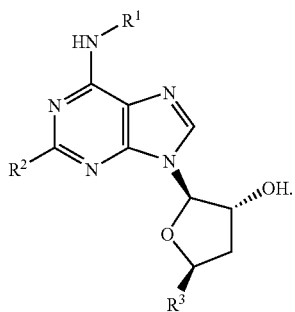

In the Formula I compounds, $R^1$ may be an optionally substituted alkyl, an optionally substituted cycloalkyl, an optionally substituted heterocyclyl, an optionally substituted aryl, or an optionally substituted heteroaryl moiety. In one embodiment, $R^1$ is an optionally substituted heterocyclic moiety. Preferred $R^1$ heterocycles are five membered heterocyclic rings having at least one nitrogen or oxygen atom. Particularly preferred $R^1$ heterocycles are optionally substituted pyrrolidine and oxolane rings.

In other embodiments, $R^1$ is an optionally substituted cycloalkyl moiety. Preferably, the cycloalkyl moiety is a five or six membered ring. In still other embodiments, $R^1$ is an optionally substituted aryl moiety, such as, but not limited to, optionally substituted phenyl and naphthyl rings.

As discussed above, the $R^1$ moiety may be optionally substituted. Typical substituents include, but are not limited to, alkyl, hydroxy, alkoxy, halo, haloalkyl, sulphonyl, and acyl, all of which may be further substituted. For example, the optional substituent on the $R^1$ moiety may be represented as R"—X—, in which R" is optionally substituted aryl or optionally substituted alkyl and X is carbonyl or sulphonyl.

$R^2$ may be hydrogen, halo, trifluoromethyl, optionally substituted acyl, or cyano. Generally, $R^2$ is a hydrogen or halogen atom such as chlorine or fluorine.

$R^3$ is hydroxymethyl or $R^4R^5N(O)C$—, in which $R^4$ and $R^5$ are independently hydrogen or optionally substituted alkyl. Typically $R^3$ is hydroxymethyl.

Synthetic Reaction Parameters

The terms "solvent", "inert organic solvent" or "inert solvent" means a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

AIBN refers to 2,2'-azobisisobutyronitrile.

HMDS refers to hexamethyldisilazane.

TMS-TF refers to trimethylsilyl triflate.

The compounds of Formula I in which $R^2$ is hydrogen are prepared as shown in Reaction Scheme I.

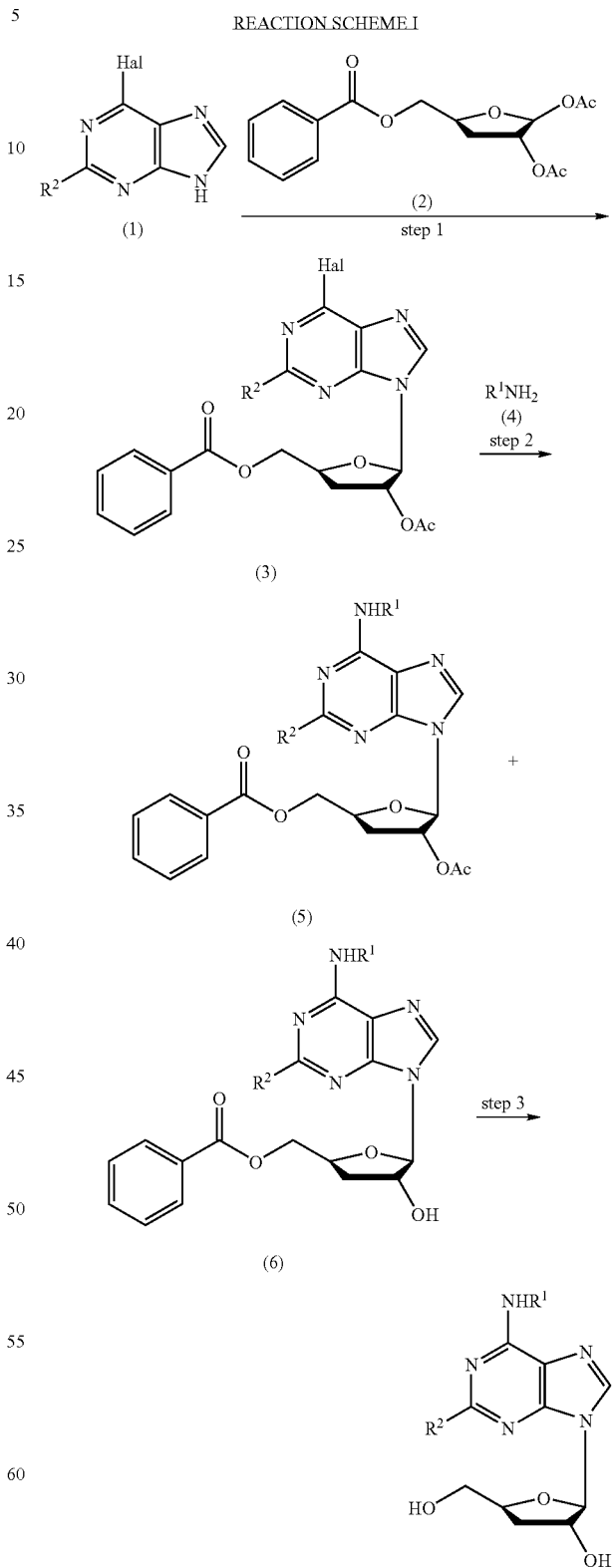

REACTION SCHEME I

Step 1. Preparation of Formula (3).

The compound of formula (3) is prepared in two steps. Firstly, a compound of formula (1) is mixed with an excess of a silylating reagent, for example hexamethyldisilazane (HMDS), and a catalyst, for example ammonium sulfate. The reaction mixture is maintained under reflux conditions for about 1–6 hours, for example about 3 hours. The excess of silylating reagent is removed under reduced pressure, and then co-evaporated with an organic solvent, for example, dry toluene.

Secondly, the residue is dissolved in an inert solvent, for example methylene chloride, and the compound of formula (2), 1,2-diO-acetyl-5-O-benzoyl-3-deoxyribofuranose, is added. The reaction mixture is stirred for about 5–30 minutes, preferably about 10 minutes, then a catalyst added, for example trimethylsilyl triflate (TMS-TF). The mixture is stirred for about 1–8 hours, for example about 3 hours, at about room temperature. The solution is made basic, for example with a saturated solution of sodium bicarbonate, and product is isolated conventionally. The compound of formula (3) may be further purified by crystallization.

Step 2. Preparation of a Mixture of Compounds of Formula (5) and Formula (6).

The compound of formula (3) is then converted to a mixture of the compounds of formulae (5) and (6) by reaction with an amine of formula $R^1NH_2$ (4), in the presence of a tertiary base, for example, triethylamine, in an inert solvent, for example methanol. The reaction is conducted at about 40–80° C., preferably at about 65° C., for about 4–24 hours, preferably about 14 hours. Additional $R^1NH_2$ may be added, in which case the reaction is continued for a further 12–36 hours. When the reaction is substantially complete, a mixture of the compounds of the formula (5) and (6) are isolated by conventional means, for example removal of the solvent under reduced pressure.

Step 3. Preparation of a Compound of Formula I

The mixture of the compounds of formula (5) and (6) is dissolved in an ammonia saturated protic solvent such as methanol or the like and stirred at about room temperature for 18–48 hours, preferably about 36 hours. When the reaction is substantially complete, the compound of Formula I is isolated and purified by conventional means, for example by chromatography and/or crystallization from a suitable solvent.

Preparation of the Starting Materials of Step 1

Starting compounds of the formula (1), are commercially available, for example from Aldrich (Milwaukee, Wis.) and from Acros Organics (Fisher, Los Angeles, Calif.).

The compound of formula (2), 1,2-di-O-acetyl-5-O-benzoyl-3-deoxyribofuranose, is prepared by means well known in the art, for example by applying the method described in *Carbohydrate Research*, 323 (2000) 226–229 but substituting ribose as the starting material in place of L-xylose.

In general, the synthesis of the compounds of formula (2) begins with protection of the 2 and 3 hydroxy groups of ribose as an acetonide. The protected ribose is then treated with benzoyl chloride in the presence of a base to form the benzoyl derivative of the hydroxymethyl moiety. The remaining 3'-hydroxy group is then reacted with thiocarbonyldiimidazole to form the imidazolethiocarbonyl derivative, which is subsequently reacted with tributyltin hydride to provide the 4-deoxy derivative. Deprotection of this compound with acid provides the desired 1,2-di-O-acetyl-5-O-benzoyl-3-deoxyribofuranose of formula (2).

Preparation of the Starting Materials of Step 2.

Many of the compounds of formula (4) are commercially available, or prepared by means well known in the art. Compounds of formula (4) where $R^1$ is a pyrrolidinyl substituted with a group R"X, in which R" is optionally substituted aryl or optionally substituted alkyl and X is carbonyl or sulphonyl are synthesized as shown in Reaction Scheme II.

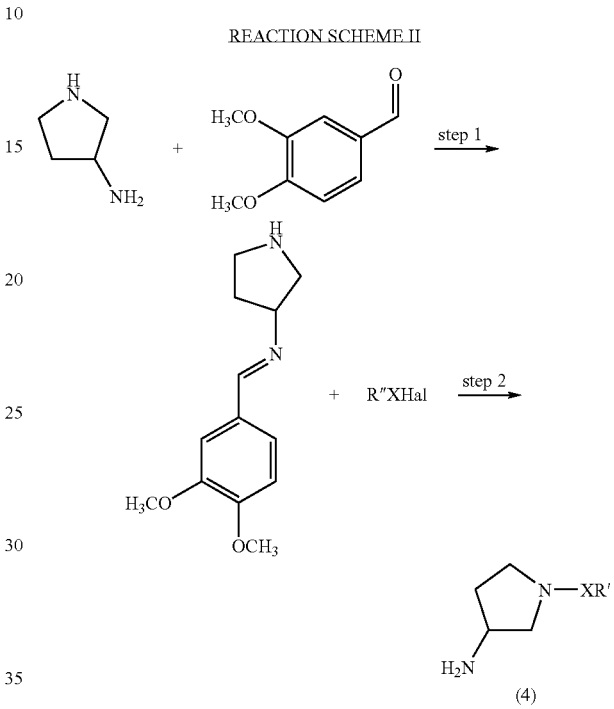

REACTION SCHEME II

Step 1. Preparation of 4-(2-aza-2-pyrrolidin-3-ylvinyl)-1,2-dimethoxybenzene

3-Aminopyrrolidine is reacted with 3-(3,4-dimethoxybenzaldehyde, which is commercially available from Aldrich (Milwaukee, Wis.) in an inert solvent, for example methanol, in the presence of a base, for example sodium carbonate, and stirred for about 4–24 hours, preferably about 12 hours, at about room temperature. When the reaction is substantially complete, 4-(2-aza-2-pyrrolidin-3-ylvinyl)-1,2-dimethoxybenzene is isolated and purified by conventional means, and used without further purification.

Step 2. Preparation of Formula (4)

4-(2-aza-2-pyrrolidin-3-ylvinyl)-1,2-dimethoxybenzene (3 mmol) is reacted with a compound of the formula R"X-Hal, in which R" is optionally substituted alkyl or optionally substituted aryl, Hal is a halogen atom such as chlorine, and X is carbonyl or sulphonyl, in an inert solvent, for example methylene chloride, in the presence of a tertiary base, for example triethylamine, or an inorganic base, for example sodium carbonate. The mixture is stirred for about 3–24 hours, preferably about 6–15 hours. When the reaction is substantially complete, the product is isolated and purified by conventional means, to provide the desired compound of formula (4).

UTILITY, TESTING AND ADMINISTRATION

General Utility

The compounds of Formula I are effective in the treatment of conditions known to respond to administration of a partial or full agonist of an $A_1$ adenosine receptor. Such conditions include, but are not limited to, acute and chronic disorders of heart rhythm, especially those diseases characterized by rapid heart rate, in which the rate is driven by abnormalities in the sinoatrial, atria, and AV nodal tissues. Such disorders include, but are not limited to, atrial fibrillation, and atrial flutter, congestive heart failure, non-insulin-dependent diabetes mellitus, hyperglycemia, epilepsy (anticonvulsant activity), and neuroprotection. $A_1$ adenosine receptor agonists also have antilipolytic effects in adipocytes, which leads to a decreased release of nonesterified fatty acids Testing Activity testing is conducted as described in those patents and literature citations referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modern Pharmaceutics", Marcel Dekker, Inc. 3$^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are for example formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. For example, for oral administration, each dosage unit contains from 10 mg to 2 g of a compound of Formula I, more for example from 10 to 700 mg, and for parenteral administration, for example from 10 to 700 mg of a compound of Formula I, more for example about 50–200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. For example the compositions are administered by the oral or nasal respiratory route for local or systemic effect. Compositions in for example pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, for example orally or nasally, from devices that deliver the formulation in an appropriate manner.

The following examples are included to demonstrate preferred embodiments of the invention. It should be appreciated by those of skill in the art that the techniques++ disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

A. Preparation of a Compound of Formula (3) in which $R^2$ is Hydrogen

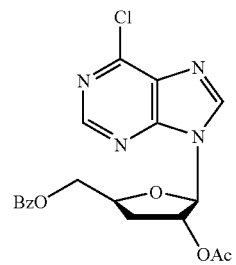

A catalytic amount of ammonium sulfate was added to a mixture of 6-chloropurine (0.56 grams, 3.62 mmol) and hexamethyldisilazane (15 mL), and the mixture was refluxed for 3 hours. The solvent was evaporated under reduced pressure, and the residue was co-evaporated with dry toluene (3×10 mL). The white solid residue was dissolved in dry methylene chloride (40 mL) and 1,2-di-O-acetyl-5-O-benzoyl-3-deoxy-ribofuranose, (1.00 g, 3.10 mmol) was added. After 10 minutes of stirring, trimethylsilyl triflate (0.8 mL) was added, and the solution stirred at room temperature for an additional 3 hours. A solution of cold, saturated sodium bicarbonate was added. After 5 minutes stirring, the organic layer was separated and the aqueous solution extracted with methylene chloride (2×30 mL). The organic layers were combined and dried over sodium sulfate, to give (5S,2R,3R)-2-(6-chloropurin-9-yl)-5-(phenylcarbonyloxymethyl) oxolan-3-yl acetate, which was purified by crystallization from methanol. The mother liquor was chromatographed on a Chromatotron, to provide additional product.

B. Preparation of Other Compounds of Formula (3) where $R^2$ is Chloro

Similarly, by replacing 6 chloropurine with 2,6 dichloropurine or other purines, the following compounds of formula (3) can be made:

(5S,2R,3R)-2-(2,6-dichloropurin-9-yl)-5-(phenylcarbonyloxymethyl)oxolan-3-yl acetate;

(5S,2R,3R)-2-(2-fluoro-6-chloropurin-9-yl)-5-(phenylcarbonyloxymethyl)oxolan-3-yl acetate;

(5S,2R,3R)-2-(2-trifluoromethyl-6-chloropurin-9-yl)-5-(phenylcarbonyloxymethyl)oxolan-3-yl acetate;

(5S,2R,3R)-2-(2-cyano-6-chloropurin-9-yl)-5-(phenylcarbonyloxymethyl)oxolan-3-yl acetate; and (5S,2R,3R)-2-(2-fluoro-6-bromopurin-9-yl)-5-(phenylcarbonyloxymethyl)oxolan-3-yl acetate.

EXAMPLE 2

A. Preparation of a Mixture of Compounds of Formula (5) and (6) where $R^1$ is 4-Hydroxycyclohexyl and $R^2$ is Hydrogen

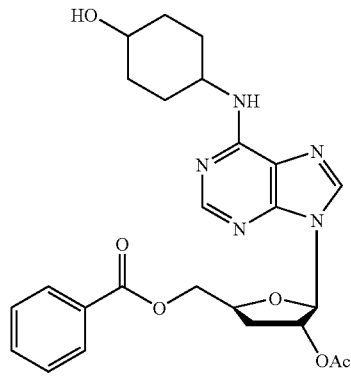

(5)

+

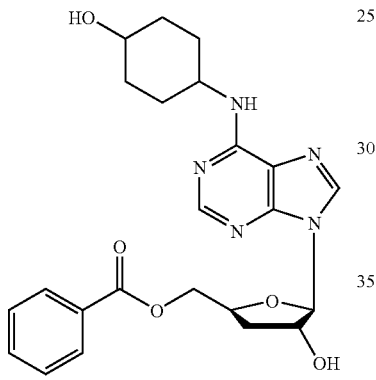

(6)

(5S,2R,3R)-2-(6-chloropurin-9-yl)-5-(phenylcarbonyloxymethyl)oxolan-3-yl acetate (200 mg., 48 mmol), a compound of formula (3), was mixed with trans-4-aminocyclohexanol hydrochloride (91 mg 0.60 mmol), a formula (4) compound, triethylamine (0.5 mL) and ethanol (20 mL), and the mixture was refluxed for 14 hours. Additional trans-4-aminocyclohexanol (30 mg, 0.2 mmol) was added, and refluxing was continued for 24 hours. The solvent was evaporated and a small amount of the mixture was purified by silica gel flash chromatography, eluting with chloroform, hexanes, and methanol (60–37–3), to obtain a mixture of (5S,2R,3R)-2-{6-[(4-hydroxycyclohexyl)amino]purin-9-yl}-5-(phenylcarbonyloxymethyl)oxolan-3-yl acetate and ((2S,5R)-4-hydroxy-5-{6-[(4-hydroxycyclohexyl)amino]purin-9-yl}oxolan-2-yl)methyl benzoate, compounds of formula (5) and (6) respectively.

B. Preparation of a Mixture of Compounds of Formula (5) and (6) where $R^1$ is other than 4-Hydroxycyclohexyl and $R^2$ is Hydrogen Similarly, following the procedure above, but replacing 4-hydroxy-cyclohexanol with other formula (4) compounds, the following mixtures of compounds of formula (5) and (6) were prepared:

2-{6-[((1R)-2-hydroxycyclohexyl)amino]purin-9-yl}(5S,2R,3R)-5-(phenylcarbonyloxymethyl)oxolan-3-yl acetate;

(5-{6-[((1S)-2-hydroxycyclohexyl)amino]purin-9-yl}(2S,4R,5R)-4-hydroxyoxolan-2-yl)methyl benzoate;

(5S,3R)-5-(phenylcarbonyloxymethyl)oxolan-3-yl 2-{6-[((3R)pyrrolidin-3-yl)amino]purin-9-yl}acetate;

(5S,3R)-5-(hydroxymethyl)oxolan-3-yl 2-{6-[((3R)pyrrolidin-3-yl)amino]purin-9-yl}acetate;

2-{6-[((3R)oxolan-3-yl)amino]purin-9-yl}(5S,2R,3R)-5-(phenylcarbonyloxymethyl)oxolan-3-yl acetate;

(5-{6-[((3R)oxolan-3-yl)amino]purin-9-yl}(2S,4R,5R)-4-hydroxyoxolan-2-yl)methyl benzoate;

(5S,2R,3R)-2-{6-[((1S,2S)-2-hydroxycyclopentyl)amino]purin-9-yl}-5-(phenylcarbonyloxymethyl)oxolan-3-yl acetate; and (5S,2R,3R)-2-{6-[((1S,2S)-2-hydroxycyclopentyl)amino]purin-9-yl}-5-(phenylcarbonyloxymethyl)oxolan-3-ol.

C. Preparation of Compounds of Formula (5) and (6) where $R^1$ is other than 4-Hydroxycyclohexyl and/or $R^2$ is other than Hydrogen Similarly, following the procedure of Example 2A above, but replacing 4-hydroxy-cyclohexanol with other formula (4) compounds and/or replacing (5S,2R,3R)-2-(6-chloropurin-9-yl)-5-(phenylcarbonyloxymethyl)oxolan-3-yl acetate with other formula (3) compounds, other compounds of formula (5) and (6) are obtained.

EXAMPLE 3

A. Preparation of (2R,3R,5R)-5-ethyl-2-{6-[(4-hydroxycyclohexyl)amino]purin-9-yl}oxolan-3-ol, a Compound of Formula I

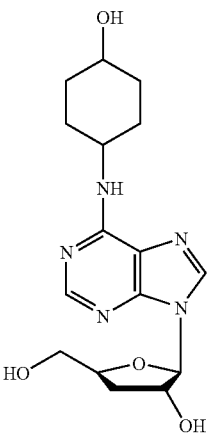

Methanol saturated with ammonia (20 mL) at 0° C. was added to a mixture of (5S,2R,3R)-2-{6-[(4-hydroxycyclohexyl)amino]purin-9-yl}-5-(benzoyloxymethyl)oxolan-3-yl acetate and (5S,2R,3R)-2-{6-[(4-hydroxycyclohexyl)amino]purin-9-yl}-5-(benzoyloxymethyl)oxolan-3-ol. The mixture was stirred at room temperature for 36 hours. The solvent was evaporated under reduced pressure, and the residue was purified on a Chromatotron to obtain (5S,2R, 3R)-2-{6-[(4-hydroxycyclohexyl)amino]purin-9-yl}-5-(hydroxymethyl)oxolan-3-ol, a compound of Formula I.

B. Preparation of other Compounds of Formula (I) where $R^1$ is Hydrogen

Similarly, following the procedure above, the following compounds of the Formula (I) were prepared:
- (5S,2R,3R)-2-{6-[(2-hydroxycyclohexyl)amino]purin-9-yl}-5-(hydroxymethyl)oxolan-3-ol;
- (5S,2R,3R)-5-hydroxymethyl-2-[6-pyrrolidin-3-ylamino)purin-9-yloxolan-3-ol;
- (5S,2R,3R)-2-{6-[(1S,2S)-2-hydroxycyclopentyl)amino]purin-9-yl}-5-(hydroxymethyl)oxolan-3-ol;
- 3-({9-[(5S,2R,3R)-3-hydroxy-5-(hydroxymethyl)oxolan-2-yl]purin-6-yl}amino)-1-benzoylpyrrolidine;
- 3-({9-[(5S,2R,3R)-3-hydroxy-5-(hydroxymethyl)oxolan-2-yl]purin-6-yl}amino)-1-(4-fluorobenzoyl)pyrrolidine;
- 3-({9-[(5S,2R,3R)-3-hydroxy-5-(hydroxymethyl)oxolan-2-yl]purin-6-yl}amino)-1-(4-cyanobenzoyl)pyrrolidine;
- 3-({9-[(5S,2R,3R)-3-hydroxy-5-(hydroxymethyl)oxolan-2-yl]purin-6-yl}amino)-1-(4-methoxybenzoyl)pyrrolidine;
- 3-({9-[(5S,2R,3R)-3-hydroxy-5-(hydroxyemthyl)oxolan-2-yl]purin-6-yl}amino)-1-(4-trifluoromethylbenzoyl)pyrrolidine;
- 3-({9-[(5S,2R,3R)-3-hydroxy-5-(hydroxymethyl)oxolan-2-yl]purin-6-yl}amino)-1-(4-ethylbenzoyl)pyrrolidine;
- 3-({9-[(5S,2R,3R)-3-hydroxy-5-(hydroxymethyl)oxolan-2-yl]purin-6-yl}amino)-1-napththoylpyrrolidine;
- 3-({9-[(5S,2R,3R)-3-hydroxy-5-(hydroxymethyl)oxolan-2-yl]purin-6-yl}amino)-2-napththoylpyrrolidine;
- 3-({9-[(5S,2R,3R)-3-hydroxy-5-(hydroxymethyl)oxolan-2-yl]purin-6-yl}amino)-1-(2-fluorobenzoyl)pyrrolidine;
- {[3-({9-[(5S,2R,3R)-3-hydroxy-5-(hydroxymethyl)oxolan-2-yl]purin-6-yl}amino)-1-(phenylsufonyl)pyrrolidine;
- {[3-({9-[(5S,2R,3R)-3-hydroxy-5-(hydroxymethyl)oxolan-2-yl]purin-6-yl}amino)-1-acetylpyrrolidine;
- 3-({9-[(5S,2R,3R)-3-hydroxy-5-(hydroxymethyl)oxolan-2-yl]purin-6-yl}amino)-1-(2-methylpropanoyl)pyrrolidine; and
- 3-({9-[(5S,2R,3R)-3-hydroxy-5-(hydroxymethyl)oxolan-2-yl]purin-6-yl}amino)-1-(heptanoylpyrrolidine.

C. Preparation of other Compounds of Formula (I) where $R^2$ is Chloro.

Similarly, by replacing (5S,2R,3R)-2-{6-[(4-hydroxycyclohexyl)amino]purin-9-yl}-5-(benzoyloxymethyl)oxolan-3-yl acetate and (5S,2R,3R)-2-{6-[(4-hydroxycyclohexyl)amino]purin-9-yl}-5-(benzoyloxymethyl)oxolan-3-ol with (2S,3R,5R)-2-{2-chloro-6-[(4-hydroxycyclohexyl)amino]purin-9-yl}-5-(phenylcarbonyloxymethyl)oxolan-3-yl acetate and ((4S,5S,2R)-5-{2-chloro-6-[(4-hydroxycyclohexyl)amino]purin-9-yl}-4-hydroxyoxolan-2-yl)methyl benzoate, the following compounds of Formula (I) were made:
- (5S,2R,3R)-2-[2-chloro-6-(pyrrolidin-3-ylamino)purin-9-yl]-5-(hydroxymethyl)oxolan-3-ol;
- (5S,2R,3R)-2-{2-chloro-6-[(2-hydroxycyclopentyl)amino]purin-9-yl}-5-(hydroxymethyl)oxolan-3-ol;
- 3-({9-[(5S,2R,3R)-3-hydroxy-5-(hydroxymethyl)oxolan-2-yl]-2-chloropurin-6-yl}amino)-1-acetylpyrrolidine; and
- 1-[3-({9-[(5S,2R,3R)-3-hydroxy-5-(hydroxymethyl)oxolan-2-yl]-2-chloropurin-6-yl}amino)-1-heptanoylpyrrolidine.

D. Preparation of Compounds of Formula (I) Varying $R^1$

Similarly, following the procedure of Example 3A above, but replacing (5S,2R,3R)-2-{6-[(4-hydroxycyclohexyl)amino]purin-9-yl}-5-(benzoyloxymethyl)oxolan-3-yl acetate and (5S,2R,3R)-2-{6-[(4-hydroxycyclohexyl)amino]purin-9-yl}-5-(benzoyloxymethyl)oxolan-3-ol with other Formula (5) and (6) compounds, other compounds of Formula (I) are obtained.

EXAMPLE 4

Conversion of a Compound of Formula I where $R^2$ is Chloro to a Compound of Formula (I) where $R^2$ is Hydrogen If desired, a compound of Formula I in which $R^2$ is chloro may be converted to a compound of Formula I in which $R^2$ is hydrogen by catalytic hydrogenation. In general, compound of Formula I in which $R^2$ is chloro is dissolved in ethanol (50 mL) and hydrogenated in the presence of a catalyst, for example palladium on carbon (50 mg), and a base, for example sodium hydroxide (1 mL, 1N) under an atmosphere of $H_2$ for 12–24 hours at 45 psi. The mixture is filtered, the solvent concentrated under reduced pressure, and the residue purified by chromatography

EXAMPLE 5

Preparation of 4-(2-aza-2-pyrrolidin-3-ylvinyl)-1,2-dimethoxybenzene

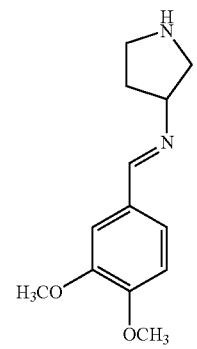

3-aminopyrrolidine dihydrochloride (1 g, 6.28 mmol), which is commercially available from TCI (Portland, Oreg.), and 3-(3,4-dimethoxybenzaldehyde (1.044 g, 6.8 mmol), which is commercially available from Aldrich (Milwaukee, Wis.) were dissolved in dry methanol (20 mL), and sodium carbonate (2 g) was added. The mixture was stirred overnight at room temperature. The product was filtered through Celite™ and the solvent evaporated under reduced pressure from the filtrate, to give a residue containing 4-(2-aza-2-pyrrolidin-3-ylvinyl)-1,2-dimethoxybenzene, which was used without further purification.

EXAMPLE 6

A. Preparation of Compounds of Formula (4) wherein X is —CO— and R'' is Phenyl

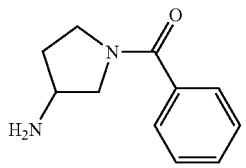

4-(2-aza-2-pyrrolidin-3-ylvinyl)-1,2-dimethoxybenzene (3 mmol) and benzoyl chloride (3.5 mmol), a compound of formula (10), were added to a mixture of dry methylene chloride (15 mL) and sodium carbonate (600 mg). The mixture was stirred for hours and then filtered through a Celite™ bed. Solvent was removed from the filtrate by evaporation, and the residue was dissolved in a mixture of methanesulfonic acid (3.84 g) in 20 mL tetrahydrofuran:water (3:1), and stirred for 60 hours. The solution was neutralized with sodium carbonate, filtered, and solvent removed from the filtrate under reduced pressure. The residue was purified on a silica gel flash chromatography column, to obtain 3-aminopyrrolidinyl phenyl ketone as an oil.

B. Preparation of Other Compounds of Formula (4) wherein X is —CO— or —SO$_2$— and R'' is Optionally Substituted Phenyl Similarly, using the method described above but replacing benzoyl chloride with other compounds of formula (10), the following compounds of formula (4) were made:
3-aminopyrrolidinyl 4-fluorophenyl ketone;
3-aminopyrrolidinyl 4-cyanophenyl ketone;
3-aminopyrrolidinyl 2-fluorophenyl ketone;
3-aminopyrrolidinyl 3-fluorophenyl ketone;
3-aminopyrrolidinyl 4-methoxyphenyl ketone;
3-aminopyrrolidinyl 4-trifluoromethylphenyl ketone;
3-aminopyrrolidinyl 4-ethylphenyl ketone;
3-aminopyrrolidinyl naphthyl ketone;
3-aminopyrrolidinyl 2-naphthyl ketone; and
1-(phenylsulfonyl)pyrrolidine-3-ylamine.

EXAMPLE 7

A. Preparation of 1-acetyl-3-aminopyrrolidine, a compound of Formula (4) where R'' is Methyl

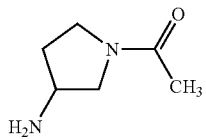

To (3,4-dimethoxy-benzylidene)-pyrrolidin-3-yl-amine (3 mmol) in dry methylene chloride (30 mL) and triethylamine (7.5 mmol) at room temperature was added acetyl chloride (3.5 mmol) dropwise. The mixture was stirred for 6 hours at room temperature, then the solvent removed under reduced pressure. The residue was dissolved in a mixture of methanesulfonic acid (3.84 g) in 20 mL tetrahydrofuran:water (3:1) and stirred for 60 hours. The solution was neutralized with solid sodium carbonate, filtered, and solvent removed from the filtrate under reduced pressure. The residue was purified by silica gel flash chromatography column, eluting firstly with CHCl$_3$—cC$_6$H$_{12}$—MeOH (85-14-1, 1.0 1) to elute the faster moving spots, and then with CHCl$_3$—MeOH—NH$_3$/MeOH (93-5-2), to obtain 1-acetyl-3-aminopyrrolidine, a compound of formula (4) as an oil.

B. Preparation of other Compounds of Formula (4) wherein X is —CO— and R'' is Alkyl Following the method described above the following compounds of formula (4) in which X is carbonyl and R'' is alkyl were made:
1-(2-methylpropanoyl)-3-aminopyrrolidine; and
1-(3-heptanoyl)-3-aminopyrrolidine.

EXAMPLE 8

All compounds of Formula I prepared as shown in the above procedures were characterized by NMR. For example:

2-{6-[((3R)oxolan-3-yl)amino]purin-9-yl}(5S,2R,3R)-5-(hydroxymethyl)oxalan-3-ol $^1$H NMR (DMSO-d$_6$) δ 2.1–2.45 (m, 6H), 3.53 (m, 1H), 3.82 (m, 1H), 3.95 (m, 1H), 4.05 (m, 1H), 4.51 (m, 1H,), 4.75 (m, 2H), 4.84 (m, 2H), 5.84 (d, J=4 Hz, 1H), 8.36 (s, 1H) 8.41 (s, 1H).

2-{6-[((1R)-4-hydroxycyclohexyl)amino]purin-9-yl}(5S,2R,3R)-5-(hydroxymethyl)oxolan-3-ol $^1$H NMR (Me$_2$SO-d$_6$): δ 1.35 (m, 4H, cyclohexyl), 1.87 (m, 5H, 4H-cyclohexyl and H-3'b), 2.26 (m, 1H, H-3'a), 3.43 (m, 2H, C<u>H</u>—OH and CH$_2$-5'), 3.70 (m, 1 H, CH$_2$-5'), 4.05 (m, 1H, CH—NH), 4.35 (m, 1H, H-4'), 4.58 (m, 2H, H-2' and OH cyclohexyl), 5.18 (t, 1H, J=5.4 Hz, OH-5'), 5.67 (d, 1H, J=4.2 Hz, OH-2'), 5.88 (d, 1H, J=2.0 Hz, H-1'), 7.58 (d, 1H, J=7.8 Hz, NH), 8.21 (s, 1H, H-2), 8.36 (s, 1H, H-8);

2-{6-[((1R)-2-hydroxycyclohexyl)amino]purin-9-yl}(5S,2R,3R)-5-(hydroxymethyl)oxolan-3-ol $^1$H NMR (Me$_2$SO-d$_6$): δ 1.25 (m, 4H, cyclohexyl), 1.65 (m, 2H, cyclohexyl), 1.94 (m, 3H, 2H-cyclohexyl and H-3'b), 2.27 (m, 1H, H-3'a), 3.47 (m, 2H, CH—OH and CH$_2$-5'), 3.74 (m, 1H, CH$_2$-5'), 3.98 (m, 1H, CH—NH), 4.38 (m, 1H, H-4'), 4.61 (m, 2H, H-2' and OH cyclohexyl), 5.21 (t, 1H, J=5.3 Hz, OH-5'), 5.68 (d, 1H, J=4.2 Hz, OH-2'), 5.88 (d, 1H, J=2.4 Hz, H-1'), 7.43 (d, 1H, J=8.1 Hz, NH), 8.19 (s, 1H, H-2), 8.37 (s, 1H, H-8);

2-{6-[((3R)pyrrolidin-3-yl)amino]purin-9-yl}(5S,2R,3R)-5-(hydroxymethyl)oxolan-3-ol $^1$H NMR (Me$_2$SO-d$_6$): δ 1.63–2.32 (m, 6H, CH$_2$-3', NH$_2$, 2H pyrr), 3.47–3.82 (m, 5H, 3H pyrr and CH$_2$-5'), 4.13 (m, 2H, CH$_2$ pyrr), 4.37 (m, 1H, H-4'), 4.54 (m, 1H, H-2'), 5.18 (m, 1H, OH-5'), 5.70 (m, 1H, OH-2'), 5.90 (d, 1H, J=2.1 Hz, H-1'), 8.21 (s, 1H, H-2), 8.36 (s, 1H, H-8).

(5S,2R,3R)-2-{6-[((1S,2S)-2-hydroxycyclopentyl)amino]purin-9-yl}-5-(hydroxymethyl)oxolan-3-ol ¹H NMR (Me₂SO-d₆): δ 1.40–2.35 (m, 8H, CH₂-3' and CH₂—CH₂—CH₂), 3.50 (m, 1H, CH₂-5'), 3.70 (m, 1H, CH₂-5'), 4.05 (m, 1H, C<u>H</u>—OH), 4.37 (m, 2H, H-4' and CH—NH), 4.58 (m, 1H, H-2'), 4.90 (d, 1H, OH cyclopentyl), 5.18 (t, 1H, J=5.5 Hz, OH-5'), 5.68 (d, 1H, J=4.3 Hz, OH-2'), 5.90 (d, 1H, J=2.0 Hz, H-1'), 7.70 (d, 1H, J=7.4 Hz, NH), 8.22 (s, 1H, H-2), 8.39 (s, 1H, H-8);

(3R)-3-({9-[(5S,2R,3R)-3-hydroxy-5-(hydroxymethyl)oxolan-2-yl]purin-6-yl}amino)pyrrolidinyl phenyl ketone ¹H NMR (DMSO d⁶): δ 1.82–2.32 (m, 4H, CH₂-3' and 2H pyrr), 3.39–3.91 (m, 6H, CH₂-5' and 4H pyrr), 4.37 (m, 1H, H-4'), 4.57 (m, 1H, H-2'), 4.77 (br m, 1H, CH—NH), 5.14 (m, 1H, OH-5'), 5.68 (m, 1H, OH-2'), 5.87+5.91 (d+d, 1H, J=2.0 Hz, H-1'), 7.39–7.59 (m, 5H, Ph), 8.12–8.32 (m, 2H, NH and H-2), 8.40+08.44 (s+s, 1H, H-8).

(3R)-3-({9-f(5S,2R,3R)-3-hydroxy-5-(hydroxymethyl)oxolan-2-yl]purin-6-yl}amino)pyrrolidinyl 4-fluorophenyl ketone ¹H NMR (DMSO d⁶): δ 1.83–2.35 (m, 4H, CH₂-3' and CH₂ pyrr), 3.40–3.92 (m, 7H, CH₂-5' and 5H pyrr), 4.38 (m, 1H, H-4'), 4.60 (m, 1H, H-2'), 4.65–4.95 (m, 1H, CH—NH), 5.16 (m, 1H, OH-5'), 5.69 (m, 1H, OH-2'), 5.83+5.92 (d+d, J=2.2 Hz, 1H, H-1'), 7.27 (m, 2H, Ph), 7.63 (m, 2H, Ph), 8.12–8.30 (m, 2H, H-2 and NH), 8.41+8.45 (s+s, 1H, H-8).

(3R)-3-({9-[(5S,2R,3R)-3-hydroxy-5-(hydroxymethyl)oxolan-2-yl]purin-6-yl}amino)pyrrolidinyl 4-cyanophenyl ketone ¹H NMR (DMSO d⁶): δ 1.86–2.34 (m, 4H, CH₂-3' and CH₂ pyrr), 3.36–3.90 (m, 7H, CH₂-5' and 5H pyrr), 4.38 (m, 1H, H-4'), 4.57 (m, 1H, H-2'), 4.65–4.93 (m, 1H, CH—NH), 5.16 (m, 1H, OH-5'), 5.68 (m, 1H, OH-2'), 5.88+5.91 (s+s, 1H, H-1'), 7.72 (m, 2H, Ph), 7.93 (m, 2H, Ph), 8.15–8.31 (m, 2H,H-2 and NH), 8.41+8.44 (s+s, 1H, H-8).

(3R)-3-({9-[(5S,2R,3R)-3-hydroxy-5-(hydroxymethyl)oxolan-2-yl]purin-6-yl}amino)pyrrolidinyl 4-methoxyphenyl ketone ¹H NMR (DMSO d⁶): δ 1.86–2.32 (m, 4H, CH₂-3' and 2H pyrr), 3.43–3.90 (m, 7H, CH₂-5' and 5H pyrr), 4.37 (m, 1H, H-4'), 4.57 (m, 1H, H-2'), 4.59–4.94 (m, 1H, CH—NH), 5.14 (m, 1H, OH-5'), 5.66 (m, 1H, OH-2'), 5.87+5.91 (s+s, 1H, H-1'), 6.96 (m, 2H), Ph), 7.52 (m, 2H, Ph), 8.10–8.33 (m, 2H, H-2 and NH), 8.40+8.43 (s+s, 1H, H-8).

(3R)-3-({9-[((5S,2R,3R)-3-hydroxy-5-(hydroxymethyl)oxolan-2-yl]purin-6-yl}amino)pyrrolidinyl 4-(trifluoromethyl)phenyl ketone ¹H NMR (DMSO d⁶): δ 1.84–2.31 (m, 4H, CH₂-3' and 2H pyrr), 3.39–3.94 (m, 7H, CH₂-5' and 5H pyrr), 4.36 (m, 1H, H-4'), 4.57 (m, 1H, H-2'), 4.65–4.96 (m, 1H, CH—NH), 5.14 (m, 1H, OH-5'), 5.67 (m, 1H, OH-2'), 5.88+5.92 (d+d, 1H, J=2.1 Hz, H-1'), 7.78 (m, 4H, Ph), 8.14–8.31 (m, 2H, H-2 and NH), 8.40+8.44 (s+s, 1H, H-8).

3(3R)-({9-[(5S,2R,3R)-3-hydroxy-5-(hydroxymethyl)oxolan-2-yl]purin-6-yl}amino)pyrrolidinyl 4-ethylphenyl ketone ¹H NMR (DMSO d⁶): δ 1.18 (m, 3H, CH₃), 1.84–2.30 (m, 4H, CH₂-3' and 2H pyrr), 2.63 (m, 2H, CH₂—CH₃), 3.30–3.91 (m, 7H, CH₂-5' and 5H pyrr), 4.36 (m, 1H, H-4'), 4.50–4.90 (m, 2H, H-2' and CH—NH), 5.13 (m, 1H, OH-5'), 5.66 (m, 1H, OH-2'), 5.87+5.91 (s+s, 1H, H-1'), 7.27 (m, 2H, Ph), 7.46 (m, 2H, Ph), 8.07–8.34 (m, 2H, H-2 and NH), 8.40+8.43 (s+s, 1H, H-8).

(3R)-3-({9-[(5S,2R,3R)-3-hydroxy-5-(hydroxymethyl)oxolan-2-yl]purin-6-yl}amino)pyrrolidinyl 2-naphthyl ketone ¹H NMR (DMSO d⁶): δ 1.80–2.37 (m, 4H, CH₂-3' and 2H pyrr), 3.03–3.98 (m, 6H, CH₂-5' and 4H pyrr), 4.36 (m, 1H, H-4'), 4.48–5.00 (m, 2H, H-2' and CH—NH), 5.16 (m, 1H, OH-5'), 5.68 (m, 1H, OH-2'), 5.86+5.93 (s+s, 1H, H-1'), 7.20–8.50 (m, 10H, Naph, NH, H-2, H-8).

(3R)-3-({9-[(5S,2R,3R)-3-hydroxy-5-(hydroxymethyl)oxolan-2-yl]purin-6-yl}amino)pyrrolidinyl 2-fluorophenyl ketone ¹H NMR (DMSO d₆): δ 1.86–2.32 (m, 4H, CH₂-3' and 2H pyrr), 3.22–3.87 (m, 6H, CH₂-5' and 4H pyrr), 4.36 (m, 1H, H-4'), 4.57 (m, 1H, H-2'), 4.69 (m, CH—NH), 5.14 (m, 1H, OH-5'), 5.67 (m, 1H, OH-2'), 5.87+5.91 (d+d, 1H, J=2.0 Hz, H-1'), 7.28 (m, 2H, Ph), 7.47 (m, 2H, Ph), 8.10–8.30 (m, 2H, H-2 and NH), 8.40+8.43 (s+s, 1H, H-8).

3-({9-[(5S,2R,3R)-3-hydroxy-5-(hydroxymethyl)oxolan-2-yl]purin-6-yl}amino)pyrrolidinyl 3-fluorophenyl ketone ¹H NMR (DMSO d⁶): δ 1.84–2.32 (m, 4H, CH₂-3' and 2H pyrr), 3.29–4.02 (m, 6H, CH₂-5' and 4H pyrr), 4.36 (m, 1H, H-4'), 4.57 (m, 1H, H-2'), 4.63–4.95 (br m, CH—NH), 5.14 (m, 1H, OH-5'), 5.68 (m, 1H, OH-2'), 5.87+5.91 (d+d, 1H, J=2.4 Hz, H-1'), 7.18–7.57 (m, 4H, Ph), 8.10–8.34 (m, 2H, H-2 and NH), 8.40+8.43 (s+s, 1H, H-8).

3(3R)-({9-[(5S,2R,3R)-3-hydroxy-5-(hydroxymethyl)oxolan-2-y]purin-6-yl}amino)-1-(phenylsulfonyl)pyrrolidine ¹H NMR (DMSO d⁶): δ 1.82–2.32 (m, 4H, CH₂-3' and 2H pyrr), 3.13–3.78 (m, 6H, CH₂-5' and 4H pyrr), 4.37 (m, 1H, H-4'), 4.57 (m, 2H, H-2' and CH—NH), 5.15 (m, 1H, OH-5'), 5.69 (m, 1H, OH-2'), 5.90 (d, 1H, J=2.1 Hz, H-1'), 7.57 (m, 3H, Ph), 7.78 (m, 2H, Ph), 7.92 (m, 1H, NH), 8.22 (s, 1H, H-2), 8.40 (s, 1H, H-8).

(3R)-3-({9-[(5S,2R,3R)-3-hydroxy-5-(hydroxymethyl)oxolan-2-yl]purin-6-yl}amino)pyrrolidinyl naphthyl ketone ¹H NMR (DMSO d⁶): δ 1.84–2.36 (m, 4H, CH₂-3' and 2H pyrr), 3.45–3.98 (m, 6H, CH₂-5' and 4H pyrr), 4.35 (m, 1H, H-4'), 4.56 (m, 1H, H-2'), 4.63–4.95 (br m, CH—NH), 5.14 (m, 1H, OH-5'), 5.67 (m, 1H, OH-2'), 5.86–5.92 (d+d, 1H, J=1.9 Hz, H-1'), 7.61 (m, 3H, naph), 7.90–8.30 (m, 6H, naph, H-2 and NH), 8.39+8.44 (s+s, 1H, H-8).

(3R)-3-({9-[(5S,2R,3R)-3-hydroxy-5-(hydroxymethyl)oxolan-2-yl]purin-6-yl}amino)-1-acetylpyrrolidine $^1$H NMR (DMSO d$^6$): δ 1.85–2.31 (m, 7H, CH$_2$-3', 2H pyrr and CH$_3$), 3.25–3.84 (m, 6H, CH$_2$-5' and 4H pyrr), 4.37 (m, 1H, H-4'), 4.57 (m, 1H, H-2'), 4.76 (br m, CH—NH), 5.16 (m, 1H, OH-5'), 5.68 (m, 1H, OH-2'), 5.90 (d, 1H, J=1.5 Hz, H-1'), 8.12 (m, 1H, NH), 8.27 (s, 1H, H-2), 8.42 (s, 1H, H-8).

1-[(3R)-3-({9-[(5S,2R,3R)-3-hydroxy-5-(hydroxymethyl)oxolan-2-yl]purin-6-yl}amino)pyrrolidinyl]-2-methylpropan-1-one $^1$H NMR (DMSO d$^6$): δ 1.00 (m, 6H, CH$_3$ i-prop), 1.86–2.32 (m, 4H, CH$_2$-3' and 2H pyrr), 3.27–3.90 (m, 6H, CH$_2$-5' and 4H pyrr), 4.37 (m, 1H, H-4'), 4.58 (m, 1H, H-2'), 4.77 (br m, CH—NH), 5.14 (t, 1H, J=5.7 Hz, OH-5'), 5.68 (m, 1H, J=4.2 Hz, OH-2'), 5.90 (s, 1H, H-1'), 8.10 (m, 1H, NH), 8.26 (s, 1H, H-2), 8.41 (s, 1H, H-8).

1-[(3R)-3-({9-[(5S,2R,3R)-3-hydroxy-5-(hydroxymethyl)oxolan-2-yl]purin-6-yl}amino)pyrrolidinyl]-2-methylpropan-1-one $^1$H NMR (DMSO d$^6$): δ 0.86 (m, 3H, CH$_3$), 1.26 (m, 6H, 3 CH$_2$ heptyl), 1.48 (m, 2H, CH$_2$ heptyl), 1.86–2.33 (m, 6H, CH$_2$-3', CH$_2$—CO, and 2H pyrr), 3.27–3.84 (m, 6H, CH$_2$-5' and 4H pyrr), 4.38 (m, 1H, H-4'), 4.58 (m, 1H, H-2'), 4.75 (br m, CH—NH), 5.16 (t, 1H, J=5.7 Hz, OH-5'), 5.69 (d, 1H, J=3.9 Hz, OH-2'), 5.91 (d, 1H, J=1.8 Hz, H-1'), 8.11 (m, 1H, NH), 8.27 (s, 1H, H-2), 8.42 (s, 1H, H-8),

2-{6-[((3R)pyrrolidin-3-yl)amino]-2-chloropurin-9-yl}(5S,2R,3R)-5-(hydroxymethyl)oxolan-3-ol $^1$H NMR (Me$_2$SO-d$_6$): δ 1.62–2.30 (m, 6H, CH$_2$-3', NH$_2$, 2H pyrr), 3.50–3.81 (m, 5H, 3H pyrr and CH$_2$-5'), 4.11 (m, 2H, CH$_2$ pyrr), 4.37 (m, 1H, H-4'), 4.49 (m, 1H, H-2'), 5.05 (t, 1H, J=5.1 Hz, OH-5'), 5.72 (d, 1H, J=3.9 Hz, OH-2'), 5.83 (d, 1H, J=1.8 Hz,H-1'), 8.40 (s, 1H, H-8).

2-{6-[((1R)-2-hydroxycyclopentyl)amino]-2-chloropurin-9-yl}(5S,2R,3R)-5-(hydroxymethyl)oxolan-3-ol $^1$H NMR (Me$_2$SO-d$_6$): δ 1.42–2.30 (m, 8H, CH$_2$-3' and (CH$_2$)$_3$), 3.54 (m, 1H, CH$_2$-5'), 3.70 (m, 1H, CH$_2$-5'), 4.06 (m, 1H, CH—OH), 4.22 (m, 1H, CH—NH), 4.37 (m, 1H, H-4'), 4.52 (m, 1H, H-2'), 4.80 (s, 1H, OH cyclopentyl), 5.04 (t, 1H, J=5.4 Hz, OH-5'), 5.70 (d, 1H, J=3.6 Hz, OH-2'), 5.83 (s, 1H, H-1'), 7.70 (d, 1H, J=7.2 Hz, NH), 8.40 s, 1H, H-8);

(3R)-3-({9-[(5S,2R,3R)-3-hydroxy-5-(hydroxymethyl)oxolan-2-yl]-2-chloropurin-6-yl}amino)-1-acetylpyrrolidine $^1$H NMR (DMSO d$^6$): δ 1.85–2.31 (m, 7H, CH$_2$-3', 2H pyrr and CH$_3$), 3.24–3.83 (m, 6H, CH$_2$-5' and 4H pyrr), 4.37 (m, 1H, H-4'), 4.52 (m, 1H, H-2'), 4.66 (br m, CH—NH), 5.04 (t, 1H, J=4.8 Hz, OH-5'), 5.68 (m, 1H, J=4.0 Hz, OH-2'), 5.84 (s, 1H, H-1'), 8.46 (s, 1H, H-8), 8.64 (m, 1H, NH).

1-[(3R)-3-({9-[(5S,2R,3R)-3-hydroxy-5-(hydroxymethyl)oxolan-2-yl]-2-chloropurin-6-yl}amino)pyrrolidinyl]heptan-1-one $^1$H NMR (DMSO d$^6$): δ 0.86 (m, 3H, CH$_3$), 1.25 (m, 6H, 3 CH$_2$ heptyl), 1.48 (m, 2H, CH$_2$ heptyl), 1.86–2.30 (m, 6H, CH$_2$-3', CH$_2$—CO, and 2H pyrr), 3.16–3.82 (m, 6H, CH$_2$-5' and 4H pyrr), 4.37 (m, 1H, H-4'), 4.51 (m, 1H, H-2'), 4.65 (br m, CH—NH), 5.05 (t, 1H, J=5.4 Hz, OH-5'), 5.67 (d, 1H, J=4.1 Hz, OH-2'), 5.84 (d, 1H, J=1.5 Hz, H-1'), 8.44 (s, 1H, H-8), 8.62 (m, 1H, NH).

EXAMPLE 9

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

EXAMPLE 10

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 11

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

EXAMPLE 12

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 13

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

EXAMPLE 14

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 15

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 16

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 17

A subcutaneous formulation may be prepared as follows:

| Ingredient | Quantity |
| --- | --- |
| Active Ingredient | 5.0 mg |
| Corn Oil | 1.0 mL |

EXAMPLE 18

An injectable preparation is prepared having the following composition:

| Ingredients | Amount |
| --- | --- |
| Active ingredient | 2.0 mg/mL |
| Mannitol, USP | 50 mg/mL |
| Gluconic acid, USP | q.s. (pH 5–6) |
| water (distilled, sterile) | q.s. to 1.0 mL |
| Nitrogen Gas, NF | q.s. |

EXAMPLE 19

A topical preparation is prepared having the following composition:

| Ingredients | grams |
| --- | --- |
| Active ingredient | 0.2–10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60 C with stirring. A sufficient quantity of water at 60 C is then added with vigorous stirring to emulsify the ingredients, and water then added q.s. 100 g.

EXAMPLE 20

Sustained Release Composition

| Ingredient | Weight Range (%) | Preferred Range (%) | Most Preferred |
| --- | --- | --- | --- |
| Active ingredient | 50–95 | 70–90 | 75 |
| Microcrystalline cellulose (filler) | 1–35 | 5–15 | 10.6 |
| Methacrylic acid copolymer | 1–35 | 5–12.5 | 10.0 |
| Sodium hydroxide | 0.1–1.0 | 0.2–0.6 | 0.4 |
| Hydroxypropyl methylcellulose | 0.5–5.0 | 1–3 | 2.0 |
| Magnesium stearate | 0.5–5.0 | 1–3 | 2.0 |

The sustained release formulations of this invention are prepared as follows: compound and pH-dependent binder and any optional excipients are intimately mixed(dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, for example sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl, methylcellulose, cationic methacrylate copolymers (dimethylaminoethyl methacrylate/methyl-butyl methacrylate copolymers-Eudragit® E-Röhm. Pharma), and the like. These film-forming agents may optionally contain colorants, plasticizers, and other supplemental ingredients.

The compressed tablets for example have a hardness sufficient to withstand 8 Kp compression. The tablet size will depend primarily upon the amount of compound in the tablet. The tablets will include from 300 to 1100 mg of compound free base. For example, the tablets will include amounts of compound free base ranging from 400–600 mg, 650–850 mg, and 900–1100 mg.

In order to influence the dissolution rate, the time during which the compound containing powder is wet mixed is controlled. For example the total powder mix time, i.e. the time during which the powder is exposed to sodium hydroxide solution, will range from 1 to 10 minutes and for example from 2 to 5 minutes. Following granulation, the particles are removed from the granulator and placed in a fluid bed dryer for drying at about 60° C.

EXAMPLE 21

Binding Assays—$DDT_1$ Cells

Cell Culture

DDT cells (hamster vas deferens smooth muscle cell line) were grown as monolayers in petri dishes using Dulbecco's Modified Eagle's Medium (DMEM) containing 2.5 µg mL$^{-1}$ amphotericin B, 100 U mL$^{-1}$ penicillin G, 0.1 mg mL$^{-1}$ streptomycin sulfate and 5% fetal bovine serum in a humidified atmosphere of 95% air and 5% $CO_2$. Cells were subcultured twice weekly by dispersion in Hank's Balanced Salt Solution (HBSS) without the divalent cations and containing 1 mM EDTA. The cells were then seeded in growth medium at a density of $1.2 \times 10^5$ cells per plate and experiments were performed 4 days later at approximately one day preconfluence.

Membrane Preparations

Attached cells were washed twice with HBSS (2×10 mL), scraped free of the plate with the aid of a rubber policeman in 5 mL of 50 mM Tris-HCl buffer pH 7.4 at 4° C. and the suspension homogenized for 10 s. The suspension was then centrifuged at 27,000×g for 10 min. The pellet was resuspended in homogenization buffer by vortexing and centrifuged as described above. The final pellet was resuspended in 1 vol of 50 mM Tris-HCl buffer pH 7.4 containing 5 mM $MgCl_2$ for $A_1$ adenosine receptor assays. For the [$^{35}$S]GTPγS binding assay the final pellet was resuspended in 50 mM Tris-HCl pH 7.4 containing 5 mM $MgCl_2$, 100 mM NaCl and 1 mM dithiothreitol. This membrane suspension was then placed in liquid nitrogen for 10 min, thawed and used for assays. The protein content was determined with a Bradford™ Assay Kit using bovine serum albumin as standard.

Competitive Binding Assay

Compounds of Formula I were assayed to determine their affinity for the $A_1$ adenosine receptor sites on the membranes of DDT cells. Briefly, 50–70 ug of membrane protein were incubated in a mixture containing 2 U/ml adenosine deaminase, 10 µM GTP-γS in 5 mM HE buffer containing 5 mM $MgCl_2$ in glass tubes Stock solutions of the compounds of the invention were serially diluted ($10^{-10}$M to $10^{-4}$M) in HE buffer or HE buffer alone (to determine total binding) and added to the incubation mixture. Finally, tritiated 8-cyclopentyladenosine ($^3$H-CPX) was added to a final concentration of 1.5 nM. After incubation at 23° C. 90 minutes, the reaction was stopped by filtration on a Brandel MR24 cell harvester and washing with ice-cold Tris-EDTA buffer (three times, approximate volume 10 ml/wash) over Whatman GF/B filters (presoaked for 1 h in 0.3% polyethylenimine to reduce non-specific binding). Filters were transferred to scintillation vials and 5 ml of Scintisafe (VWR, Brisbane, Calif.) was added. The amount of radioactivity retained on the filters was determined by liquid scintillation spectrometry. Protein determinations were by the method of Bradford (1976. *Anal. Biochem.* 72:248) using bovine serum albumin as the standard.

The compounds of Formula I were shown to be of high, medium, or low affinity for the $A_1$ adenosine receptor in this assay. The Ki (low) values for several of the compounds of the invention are presented in Table 1 below.

preliminary experiments, it was found that 10 μM GDP gave the optimal stimulation of CPA dependent [$^{35}$S]GTPγS binding and this concentration was therefore used in all studies. In saturation experiments, 0.5 nM [$^{35}$S]GTPγS was incubated with 0.5–1000 nM GTPγS. At the end of the incubation, each suspension was filtered and the retained radioactivity determined as described above.

The compounds of Formula I were shown to be partial or full agonists of the $A_1$ adenosine receptor in this assay.

TABLE 1

KI (LOW) VALUES

| COMPOUND | CVT No. | ki low (nM) |
|---|---|---|
| 2-{6-[((3R)oxolan-3-yl)amino]purin-9-yl}(5S,2R,3R)-5-(hydroxymethyl)oxolan-3-ol | 3454 | 1000 |
| 2-{6-[((1R)-2-hydroxycyclohexyl)amino]purin-9-yl}(5S,2R,3R)-5-(hydroxymethyl)oxolan-3-ol | 4621 | >5000 |
| 2-{6-[((1R)-2-hydroxycyclohexyl)amino]purin-9-yl}(5S,2R,3R)-5-(hydroxymethyl)oxolan-3-ol | 4622 | 4440/2943 |
| (5S,2R,3R)-2-{6-[((1S,2S)-2-hydroxycyclopentyl)amino]purin-9-yl}-5-(hydroxymethyl)oxolan-3-ol | 4625 | 4087/3686 |
| (3R)-3-({9-[(5S,2R,3R)-3-hydroxy-5-(hydroxymethyl)oxolan-2-yl]purin-6-yl}amino)pyrrolidinyl 4-fluorophenyl ketone | 4607 | >5000 |
| 4-{[(3R)-3-({9-[(5S,2R,3R)-3-hydroxy-5-(hydroxymethyl)oxolan-2-yl]purin-6-yl}amino)pyrrolidinyl]carbonyl}benzenecarbonitrile | 4608 | >5000 |
| (3R)-3-({9-[(5S,2R,3R)-3-hydroxy-5-(hydroxymethyl)oxolan-2-yl]purin-6-yl}amino)pyrrolidinyl 4-methoxyphenyl ketone | 4609 | >5000 |
| (3R)-3-({9-[(5S,2R,3R)-3-hydroxy-5-(hydroxymethyl)oxolan-2-yl]purin-6-yl}amino)pyrrolidinyl 4-(trifluoromethyl)phenyl ketone | 4610 | >5000 |
| (3R)-3-({9-[(5S,2R,3R)-3-hydroxy-5-(hydroxymethyl)oxolan-2-yl]purin-6-yl}amino)pyrrolidinyl 4-ethylphenyl ketone | 4611 | >5000 |
| (3R)-3-({9-[(5S,2R,3R)-3-hydroxy-5-(hydroxymethyl)oxolan-2-yl]purin-6-yl}amino)pyrrolidinyl 2-naphthyl ketone | 4612 | >5000 |
| (3R)-3-({9-[(5S,2R,3R)-3-hydroxy-5-(hydroxymethyl)oxolan-2-yl]purin-6-yl}amino)pyrrolidinyl 3-fluorophenyl ketone | 4613 | >5000 |
| (3R)-3-({9-[(5S,2R,3R)-3-hydroxy-5-(hydroxymethyl)oxolan-2-yl]purin-6-yl}amino)pyrrolidinyl naphthyl ketone | 4627 | 1914/2556 |
| (3R)-3-({9-[(5S,2R,3R)-3-hydroxy-5-(hydroxymethyl)oxolan-2-yl]purin-6-yl}amino)pyrrolidinyl 2-fluorophenyl ketone | 4606 | 2840 |
| (3R)-3-({9-[(5S,2R,3R)-3-hydroxy-5-(hydroxymethyl)oxolan-2-yl]purin-6-yl}amino)-1-(phenylsulfonyl)pyrrolidine | 4629 | >5000 |
| (3R)-3-({9-[(5S,2R,3R)-3-hydroxy-5-(hydroxymethyl)oxolan-2-yl]purin-6-yl}amino)-1-acetylpyrrolidine | 4617 | >5000 |
| 1-[(3R)-3-({9-[(5S,2R,3R)-3-hydroxy-5-(hydroxymethyl)oxolan-2-yl]purin-6-yl}amino)pyrrolidinyl]-2-methylpropan-1-one | 4614 | >5000 |
| 2-{6-[((1R)-2-hydroxycyclopentyl)amino]-2-chloropurin-9-yl}(5S,2R,3R)-5-(hydroxymethyl)oxolan-3-ol | 4626 | 4008/3498 |

EXAMPLE 22

[$^{35}$S]GTPγS Binding Assays $A_1$ adenosine receptor agonist stimulated [$^{35}$S]GTPγS binding was determined by a modification of the method described by Gierscikik et al. (1991) and Lorenzen et al. (1993). Membrane protein (30–50 μg) was incubated in a volume of 0.1 mL containing 50 mM Tris-HCl buffer pH 7.4, 5 mM $MgCl_2$, 100 mM NaCl, 1 mM dithiothreitol, 0.2 units $mL^{-1}$ adenosine deaminase, 0.5% BSA, 1 mM EDTA, 10 mM GDP, 0.3 nM [$^{35}$S]GTPγS and with or without varying concentrations of CPA for 90 min at 30° C. Nonspecific binding was determined by the addition of 10 μM GTPγS. Agonist stimulated binding was determined as the difference between total binding in the presence of CPA and basal binding determined in the absence of CPA. Previous reports have shown that agonist stimulated [$^{35}$S]GTPγS binding was dependent on the presence of GDP (Gierschik et al., 1991; Lorenzen et al., 1993; Traynor & Nahorski, 1995). In

EXAMPLE 23 cAMP Assay

A scintillation proximity assay (SPA) using rabbit antibodies directed at cAMP using an added tracer of adenosine 3',5'-cyclic phosphoric acid 2'-O-succinyl-3-[$^{125}$I]iodotyrosine methyl ester and fluoromicrospheres containing anti-rabbit specific antibodies as described by Amersham Pharmacia Biotech (Biotrak cellular communication assays). Briefly, $DDT_1$ cells were cultured in clear bottomed 96 well microtiter plates with opaque wells at concentrations between $10^4$ to $10^6$ cells per well in 40 μl of HBSS at 37° C. (5% $CO_2$ and 95% humidity). The partial or full $A_1$ agonists (5 μl) of this invention were incubated at various concentrations with the $DDT_1$ cells in the presence of rolipram (50 μM), and 5 μM forskolin for 10 min at 37° C. The cells were immediately lysed by treatment 5 μl of 10% dodecyltrimethylammonium bromide followed by shaking using microplate shaker. After incubation of the plate for 5 minutes, an immunoreagent solution (150 μl containing equal volumes of tracer, antiserum, and SPA fluorospheres) was added to

What we claimed is:
1. A compound of Formula I:

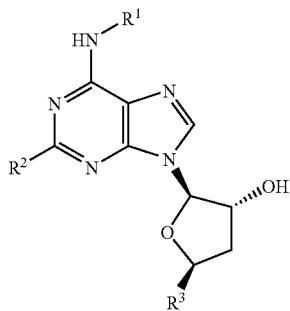

wherein:
R¹ is a cycloalkyl group having from 3–20 carbon atoms which is substituted by hydroxyl, or pyrrolidinyl N-substituted by —X—R", wherein X is carbonyl or sulphonyl, and R" is phenyl optionally substituted by methyl, ethyl, halo, trifluoromethyl, or methoxy, or R" is naphthyl, or R" is lower alkyl;
R² is hydrogen, halogen, trifluoromethyl, or cyano;
R³ is hydroxymethyl or R⁴R⁵N(O)C—, in which R⁴ and R⁵ are independently hydrogen or lower alkyl.

2. The compound of claim 1, wherein R³ is hydroxymethyl.

3. The compound of claim 2, wherein R¹ is a cycloalkyl group having from 3–20 carbon atoms which is substituted by hydroxyl.

4. The compound of claim 3, wherein R² hydrogen or halogen.

5. The compound of claim 4, wherein the compound is selected from the group consisting of:
2-{6-[((1R)-2-hydroxycyclohexyl)amino]purin-9-yl}(5S,2R,3R)-5-(hydroxymethyl)oxolan-3-ol;
2-{6-[((1R)-4-hydroxycyclohexyl)amino]purin-9-yl}(5S,2R,3R)-5-(hydroxymethyl)oxolan-3-ol;
(5S,2R,3R)-2-{6-[((1S,2S)-2-hydroxycyclopentyl)amino]purin-9-yl}-5-(hydroxymethyl)oxolan-3-ol; and
(2-{6-[((1R)-2-hydroxycyclopentyl)amino]-2-chloropurin-9-yl}(5S,2R,3R)-5-(hydroxymethyl)oxolan-3-ol.

6. The compound of claim 2, wherein R¹ is pyrrolidinyl N-substituted by—X—R".

7. The compound of claim 6, wherein R" is phenyl optionally substituted by methyl, ethyl, halo, trifluoromethyl, or methoxy.

8. The compound of claim 7, wherein the compound is selected from the group consisting of:
(3R)-3-({9-[(5S,2R,3R)-3-hydroxy-5-(hydroxymethyl)oxolan-2-yl]purin-6-yl}amino)pyrrolidinyl phenyl ketone;
(3R)-3-({9-[(5S,2R,3R)-3-hydroxy-5-(hydroxymethyl)oxolan-2-yl]purin-6-yl}amino)pyrrolidinyl4-fluorophenylketone;
4-{[(3R)-3-({9-[(5S,2R,3R)-3-hydroxy-5-(hydroxymethyl)oxolan-2-yl]purin-6-yl}amino)pyrrolidinyl]carbonyl}benzenecarbonitrile;
(3R)-3-({9-[(5S,2R,3R)-3-hydroxy-5-(hydroxymethyl)oxolan-2-yl]purin-6-yl}amino)pyrrolidinyl4-methoxyphenylketone;
(3R)-3-({9-[(5S,2R,3R)-3-hydroxy-5-(hydroxymethyl)oxolan-2-yl]purin-6-yl}amino)pyrrolidinyl4-(trifluoromethyl)phenylketone;
(3R)-3-({9-[(5S,2R,3R)-3-hydroxy-5-(hydroxymethyl)oxolan-2-yl]purin-6-yl}amino)pyrrolidinyl4-ethylphenylketone;
(3R)-3-({9-[(5S,2R,3R)-3-hydroxy-5-(hydroxymethyl)oxolan-2-yl]purin-6-yl}amino)pyrrolidinyl3-fluorophenylketone;
(3R)-3-({9-[(5S,2R,3R)-3-hydroxy-5-(hydroxymethyl)oxolan-2-yl]purin-6-yl}amino)-1-(phenylsulfonyl)pyrrolidine; and
(3R)-3-({9-[(5S,2R,3R)-3-hydroxy-5-(hydroxymethyl)oxolan-2-yl]purin-6-yl}amino)pyrrolidinyl2-fluorophenylketone.

9. The compound of claim 6, wherein R" is naphthyl.

10. The compound of claim 9, wherein the compound is selected from the group consisting of:
(3R)-3-({9-[(5S,2R,3R)-3-hydroxy-5-(hydroxymethyl)oxolan-2-yl]purin-6-yl}amino)pyrrolidinyl2-naphthylketone; and
(3R)-3-({9-[(5S,2R,3R)-3-hydroxy-5-(hydroxymethyl)oxolan-2-yl]purin-6-yl}amino)pyrrolidinyl naphthylketone.

11. The compound of claim 6, wherein R" is lower alkyl.

12. The compound of claim 11, wherein the compound is selected from the group consisting of:
(3R)-3-({9-[(5S,2R,3R)-3-hydroxy-5-(hydroxymethyl)oxolan-2-yl]purin-6-yl}amino)-1-acetylpyrrolidine;
1-[(3R)-3-({9-[(5S,2R,3R)-3-hydroxy-5-(hydroxymethyl)oxolan-2-yl]purin-6-yl}amino)pyrrolidinyl]-2-methylpropan-1-one;
1-[(3R)-3-({9-[(5S,2R,3R)-3-hydroxy-5-(hydroxymethyl)oxolan-2-yl]purin-6-yl}amino)pyrrolidinyl]heptan-1-one;
(3R)-3-({9-[(5S,2R,3R)-3-hydroxy-5-(hydroxymethyl)oxolan-2-yl]-2-chloropurin-6-yl}amino)-1-acetylpyrrolidine; and
1-[(3R)-3-({9-[(5S,2R,3R)-3-hydroxy-5-(hydroxymethyl)oxolan-2-yl]-2-chloropurin-6-yl}amino)pyrrolidinyl]heptan-1-one.

13. The compound of claim 2, wherein the R¹ moiety is an oxolanyl moiety.

14. The compound of claim 13, wherein the compound is 2-{6-[((3R)oxolan-3-yl)amino]purin-9-yl}(5S,2R,3R)-5-(hydroxymethyl)oxolan-3-ol.

15. A pharmaceutical composition comprising at least one pharmaceutically acceptable excipient and a compound of claim 1.

* * * * *